(12) United States Patent
Lorio et al.

(10) Patent No.: US 10,045,858 B2
(45) Date of Patent: Aug. 14, 2018

(54) INTERVERTEBRAL DEVICE AND METHODS OF USE

(71) Applicants: Morgan Packard Lorio, Bristol, TN (US); Thomas Purcell, Del Mar, CA (US)

(72) Inventors: Morgan Packard Lorio, Bristol, TN (US); Thomas Purcell, Del Mar, CA (US)

(73) Assignee: Morgan Packard Lorio

(*) Notice: Subject to any disclaimer, the term of this patent is extended or adjusted under 35 U.S.C. 154(b) by 78 days.

(21) Appl. No.: 15/218,295

(22) Filed: Jul. 25, 2016

(65) Prior Publication Data

US 2016/0331547 A1    Nov. 17, 2016

Related U.S. Application Data

(62) Division of application No. 13/252,427, filed on Oct. 4, 2011, now Pat. No. 9,408,710.

(60) Provisional application No. 61/389,862, filed on Oct. 5, 2010.

(51) Int. Cl.
*A61F 2/44* (2006.01)
*A61F 2/28* (2006.01)
*A61F 2/30* (2006.01)

(52) U.S. Cl.
CPC ............ *A61F 2/4455* (2013.01); *A61F 2/442* (2013.01); *A61F 2/447* (2013.01); *A61F 2002/2817* (2013.01); *A61F 2002/2835* (2013.01); *A61F 2002/30471* (2013.01); *A61F 2002/30579* (2013.01); *A61F 2002/30673* (2013.01); *A61F 2002/30841* (2013.01); *A61F 2002/30904* (2013.01); *A61F 2002/448* (2013.01); *A61F 2002/4415* (2013.01); *A61F 2002/4475* (2013.01); *A61F 2210/0071* (2013.01); *A61F 2220/0016* (2013.01); *A61F 2310/00017* (2013.01); *A61F 2310/00023* (2013.01); *A61F 2310/00161* (2013.01)

(58) Field of Classification Search
CPC ...... A61F 2/4611; A61F 2/442; A61F 2/4425; A61F 2002/4445
USPC .................... 623/17.11–17.16; 606/246–249
See application file for complete search history.

(56) References Cited

U.S. PATENT DOCUMENTS 6,039,761 A * 3/2000 Li ..................... A61B 17/70
                                                  623/17.16
2008/0243255 A1* 10/2008 Butler ................ A61F 2/4465
                                                  623/17.16

\* cited by examiner

*Primary Examiner* — Julianna N Harvey
*Assistant Examiner* — Christina Negrellirodrigue
(74) *Attorney, Agent, or Firm* — Michael R Shevlin

(57) ABSTRACT

An intervertebral device comprises a plurality of struts that are rotatably associated with each adjacent strut to form a modifiable inner volume V for bone graft containment.

27 Claims, 10 Drawing Sheets

INTERVERTEBRAL DEVICE AND METHODS OF USE

CROSS-REFERENCE TO RELATED APPLICATIONS

The present application is a divisional application of U.S. patent application Ser. No. 13/252,427, filed Oct. 4, 2011, which claims priority to U.S. Provisional Patent Application No. 61/389,862, filed Oct. 5, 2010, the entire contents of both of which are hereby expressly incorporated by reference.

RELATED APPLICATION

This application is related to U.S. patent application Ser. No. 13/248,747, filed Sep. 29, 2011, titled Minimally Invasive Intervertebral Systems and Methods, which is incorporated herein by reference.

FIELD

The present invention relates generally to a device for treating intervertebral injuries and, more specifically relates to a minimally invasive intervertebral implant.

BACKGROUND

Vertebrae are the individual irregular bones that make up the spinal column (aka ischis) a flexuous and flexible column. There are normally thirty-three vertebrae in humans, including the five that are fused to form the sacrum (the others are separated by intervertebral discs) and the four coccygeal bones which form the tailbone. The upper three regions comprise the remaining 24, and are grouped under the names cervical (7 vertebrae), thoracic (12 vertebrae) and lumbar (5 vertebrae), according to the regions they occupy. This number is sometimes increased by an additional vertebra in one region, or it may be diminished in one region, the deficiency often being supplied by an additional vertebra in another. The number of cervical vertebrae is, however, very rarely increased or diminished.

A typical vertebra consists of two essential parts: an anterior (front) segment, which is the vertebral body; and a posterior part—the vertebral (neural) arch—which encloses the vertebral foramen. The vertebral arch is formed by a pair of pedicles and a pair of laminae, and supports seven processes, four articular, two transverse, and one spinous, the latter also being known as the neural spine.

When the vertebrae are articulated with each other, the bodies form a strong pillar for the support of the head and trunk, and the vertebral foramina constitute a canal for the protection of the medulla spinalis (spinal cord), while between every pair of vertebrae are two apertures, the intervertebral foramina, one on either side, for the transmission of the spinal nerves and vessels.

Conventional spinal spacer assemblies are used in spinal fusion procedures to repair damaged or incorrectly articulating vertebrae. Spinal fusion employs the use of spacer assemblies having a hollow mesh spacer tube and end caps that space apart and fuse together adjacent vertebrae. These mesh spacer tubes are often formed of titanium and are available in varying shapes and sizes. In addition, they can be trimmed on site by the surgeon to provide a better individual fit for each patient. Conventional spinal spacer assemblies come in different cross sections. These spacer assemblies are generally hollow and include openings in the side thereof to provide access for bone to grow and fuse within the mesh tube. The current intervertebral or interbody devices are designed using 3 major principles; the anatomical limitations of the surgical approach, optimization of bone graft volume to promote bony fusion, and optimization of the device contact with the vertebral endplates to resist subsidence. The current devices are generally static in that they cannot change shape or volume, thus they are limited by the anatomy and technique, and therefore they do not provide optimal bone graft volume or surface contact. The present invention attempts to solve these problems as well as others.

SUMMARY OF THE INVENTION

Provided herein are systems, methods and apparatuses for an intervertebral device. The intervertebral device generally comprises a plurality of struts, wherein each adjacent strut is rotatably associated with each adjacent strut to form a modifiable inner volume V for bone graft containment when the intervertebral device is in an expanded state, and whereby the inner volume V is enclosed by the plurality of struts.

The method of using an intervertebral device generally comprising the steps of: preparing an intervertebral disc space by removing a portion of the annulus, evacuating the nucleus, and then removing the cartilaginous endplates; rotating the intervertebral device about its transverse axis and placing the intervertebral disc into the intervertebral disc space with the width TT of the intervertebral device parallel to the vertebral endplates; rotating the intervertebral device 90 degrees about its transverse axis to increase the height of the intervertebral disc space; expanding the intervertebral device to increase the inner volume V enclosed within the plurality of struts, such that the intervertebral device is opened; and filling the inner volume V with bone graft material to permit bone fusion between adjacent vertebrae.

The methods, systems, and apparatuses are set forth in part in the description which follows, and in part will be obvious from the description, or can be learned by practice of the systems, methods, and apparatuses. The advantages of the systems, methods, and apparatuses will be realized and attained by means of the elements and combinations particularly pointed out in the appended claims. It is to be understood that both the foregoing general description and the following detailed description are exemplary and explanatory only and are not restrictive of the systems, methods, and apparatuses, as claimed.

BRIEF DESCRIPTION OF THE FIGURES

In the accompanying figures, like elements are identified by like reference numerals among the several preferred embodiments of the present invention.

The foregoing and other features and advantages of the invention are apparent from the following detailed description of exemplary embodiments, read in conjunction with the accompanying drawings; wherein like structural or functional elements may be designated by like reference numerals.

DETAILED DESCRIPTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Figure 1A:
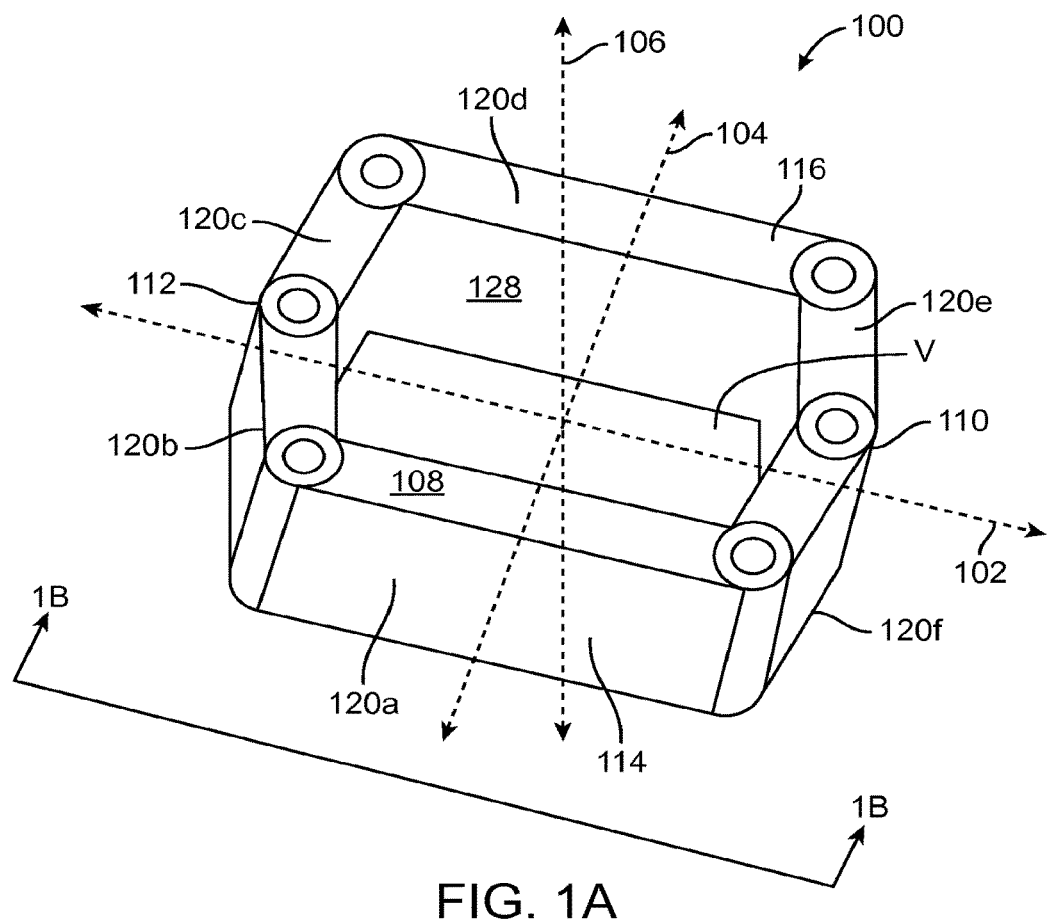
FIG. 1A is a perspective view of one embodiment of the intervertebral device in the expanded state.
Figure 1B:
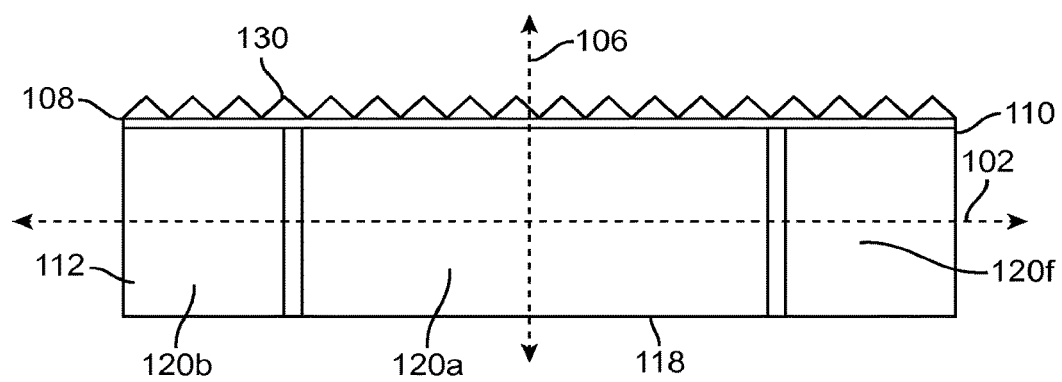
FIG. 1B is a side view of one embodiment of the intervertebral device taken along lines 1B-1B as shown in FIG. 1A.

Generally speaking, the intervertebral device 100 comprises a plurality of struts 120 that are rotatably associated with each adjacent strut 120 to form a modifiable inner volume V for bone graft containment, as shown in FIG. 1A. The intervertebral device 100 includes an expanded state, whereby the inner volume V is enclosed by the plurality of struts 120. The intervertebral device 100 generally includes a longitudinal axis 102 running along the proximal portion 110 to the distal portion 112 of the intervertebral device 100. The intervertebral device 100 generally includes a transverse axis 104, generally running along the left portion 114 to the right portion 116. The plurality of struts 210 rotatably associate with each adjacent strut 120 and rotate to expand or contract the modifiable inner volume V generally along at least the longitudinal axis 102 and/or the transverse axis 104. The intervertebral device 100 includes an anterior-posterior axis 106, which generally runs along the anterior surface 108 to the posterior surface 118, as shown in FIG. 1B. The modifiable inner volume V generally runs from the anterior surface 108 to the posterior surface 118 when the intervertebral device 100 is in an expanded state. The modifiable inner volume V provides an optimal bone graft volume and surface contact area for adjacent vertebra on the anterior surface 108 and the posterior surface 118 of the intervertebral device 100. When in the expanded state, the plurality of struts 120 is preferably static in relation to adjacent struts 120. In one embodiment, a bone graft material is placed into the inner volume V, the bone graft will generally create an outward force on the intervertebral device 100 so it will not collapse or deform to an unexpanded or closed state.

The intervertebral device 100 may include any number of struts 120 that may form a modifiable inner volume V by way of rotation or pivoting of adjacent struts 120 generally along the longitudinal axis 102 and/or the transverse axis 104 to the expanded state. Although six struts 120 are shown in FIG. 1A, the intervertebral device may include any number of struts, including, but not limited to, at least three struts, at least four struts, at least five struts, at least seven struts, at least eight struts, at least nine struts, at least ten struts, or at least between about 2 and 20 struts. The number of struts 120 selected for the intervertebral device may be selected upon the particular application for disc replacement, bone grafting, or to best match the anatomy of the adjacent vertebra. FIG. 1A shows six struts for the intervertebral device 100 comprising a first strut 120a, a second strut 120b, a third strut 120c, a fourth strut 120d, a fifth strut 120e, and a sixth strut 120f, wherein each adjacent strut is rotatably associate with adjacent struts generally along the longitudinal axis and/or transverse axis. Generally, the second strut 120b and the third strut 120c are positioned on the distal end 112 of the intervertebral device 100, while the fifth strut 120e and the sixth strut 120f are positioned on the proximal end 110. Each adjacent strut is rotatably associated with each other.

Alternatively, the anterior surface 108 and/or the posterior surface 118 include a roughed or teethed surface 130 to grip the plates of the vertebra, as shown in FIG. 1B. The teethed surface may be spaced throughout the anterior surface 108 and the posterior surface 118 of the struts 120, which can be configured to have a variable thickness, height, and width, as well as angle of orientation with respect to the anterior and poster portions 108 and 118. The teethed surface 130 can be further configured to provide additional support after the spinal spacer 100 is implanted in the vertebrae of the patient. The teethed surface 130 can reduce movement of the intervertebral device 100 in the vertebrae and create additional friction between the vertebrae and the intervertebral device 100. If more than one intervertebral device 100 is implanted in the vertebrae of the patient, the teethed surface 130 of one intervertebral device 100 can be configured to interact and/or mate with teeth of another intervertebral device, thereby creating stacked intervertebral devices. Such interaction can be useful, when multiple intervertebral devices are needed to be implanted into the vertebrae. The teethed surface 130 can be configured to have a shape of triangular protrusions extending away from the surfaces of the top and bottom portions of the spinal spacer 100. The triangular protrusions can be configured to be right-angled isosceles triangles. The triangular protrusions can be any size and shape triangles are not necessarily limited to the right-angled isosceles triangles. Further, the triangular protrusions can be configured to protrude a distance away from the anterior surface or posterior surface (whether top or bottom surfaces) of the intervertebral device 100, preferably about 0.03 millimeters. The triangular protrusions can also be spaced apart a distance D, preferably about 0.1 mm. As can be understood by one skilled in the art, the teethed surface 130 can be configured to have any shape, size, or orientation as well as can protrude any distance away from the surfaces of the spinal spacer and can have any distance between them.

Figure 1C:
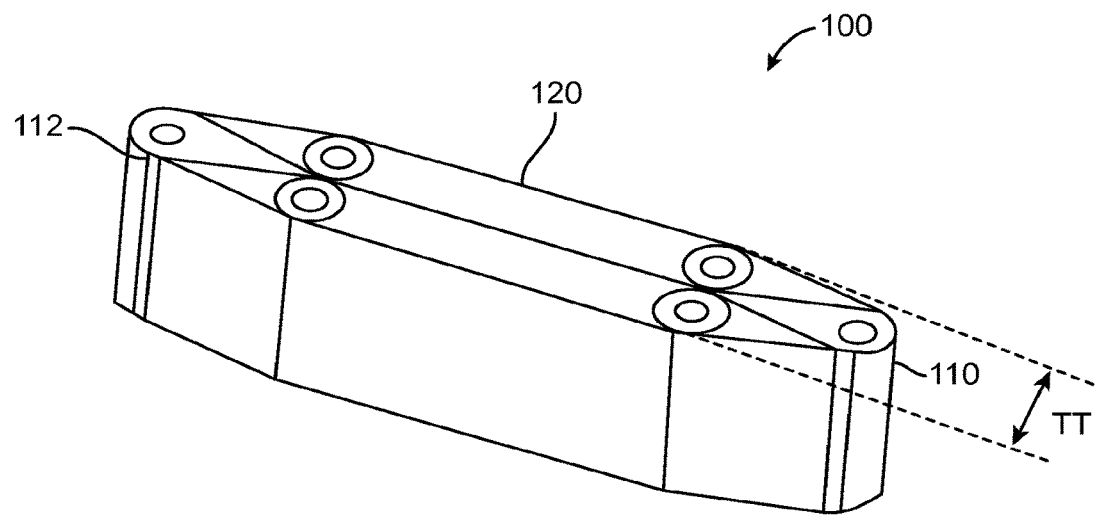
FIG. 1C is a perspective view of one embodiment of the intervertebral device in the closed state or with a substantially zero inner volume V.

As shown in FIG. 1C, the intervertebral device 100 may include a modifiable inner volume V of substantially zero when the intervertebral device 100 is in the closed state, and when the plurality of adjacent struts 120 rotate towards the interior faces of the struts 120. The intervertebral device 100 includes a zero volume state or closed state when the struts 120 are closed upon each other or the interior faces 128 of the struts face and abut the interior face of adjacent struts. As such, the intervertebral device 100 includes thickness TT profile when in the closed state. The thickness TT profile may be selected to approximate the intervertebral space between adjacent vertebrae that may be damaged or incorrectly articulating vertebrae. Preferably, the distal and proximal ends 112 and 110 of the intervertebral device 100 are tapered, such that intervertebral device 100 is minimally invasive, easily inserted through an incision site or retracted tissue, or easily displaces damaged intervertebral spaces by wedging between damaged adjacent vertebrae. The tapered distal and proximal ends 112 and 110 may be at angle with respect to longitudinal axis 102.

Figure 2A:
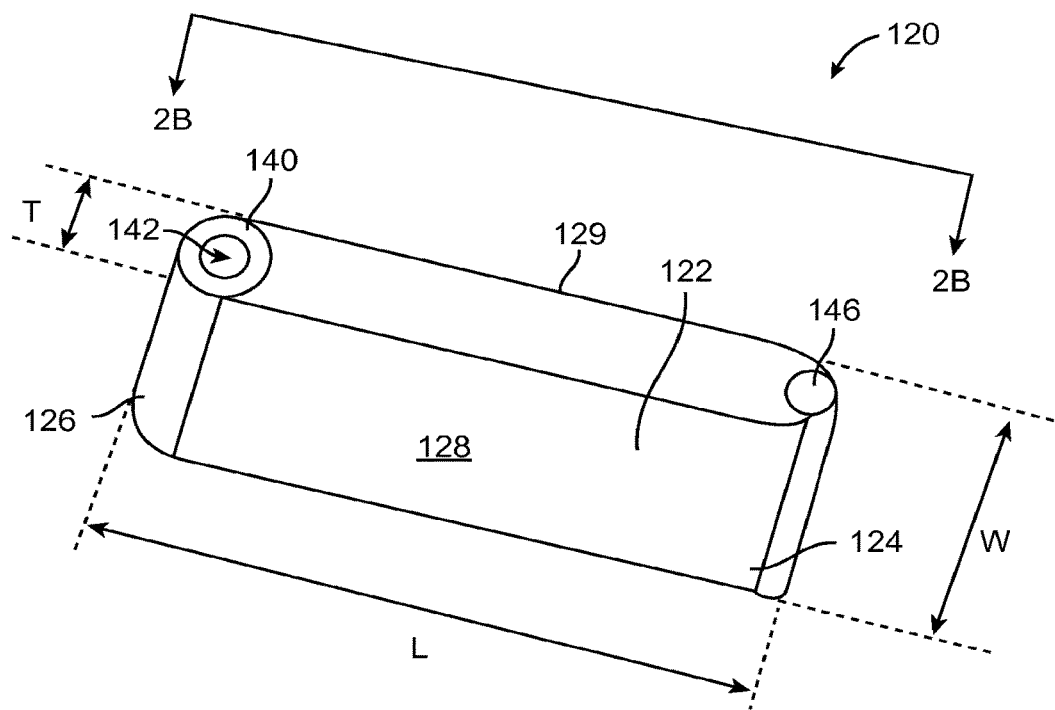
FIG. 2A is a perspective view of one embodiment of the strut.
Figure 2B:
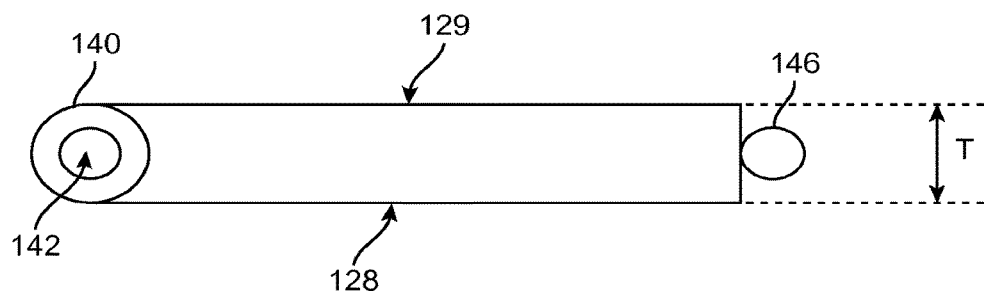
FIG. 2B is a top view of one embodiment of the strut taken along lines 2B-2B as shown in FIG. 2A.

As shown in FIG. 2A, each strut 120 includes a longitudinal body member 122 extending from a first end 124 and a second end 126, which generally runs along the longitudinal axis or length of the strut 120. Each adjacent strut 120 is rotatably associated with adjacent struts 120 by the first end 124 of a first strut rotatably associating with the second end 126 of a second strut, and the second end 126 of the first strut rotatably associating with the first end 124 of a third struts, accordingly. The struts 120 include an interior face 128 and an exterior face 129, as shown in FIG. 2B, wherein, generally, the interior face 128 faces the inner volume V. In one embodiment for rotatably associating adjacent struts 120, the second end 126 includes a pivot pin 146 and the first end includes a circular housing 140, such that when each strut 120 rotatably connects to an adjacent strut, the pivot pin 146 sits within the circular housing 140, as shown in FIG. 2A. The circular housing 140 includes a circular lumen 142 that approximates the size or circumference of the pivot pin 146. The pivot pin 146 is a substantially circular pin with a cylindrical shaft. The pivot pin 146 or the circular lumen 142 may include lubrication to allow for pivoting or rotation of the adjacent struts 120. The pivot pin 146 may be locked into place once adjacent struts are rotated to form the inner volume V of choice, by way of a screw, bolt, or fastener within the pivot pin 146.

As shown in FIG. 2A, each strut 120 includes a width W, which extends from the anterior surface to the posterior surface of the strut 120. Preferably, the width W may be selected based upon the particular vertebra that needs to resist subsistence or shortening of the intervertebral disc space. Alternatively, the width W may be selected for the amount of bone that must be grafted between adjacent vertebrae. For example, each intervertebral space includes a varied width, and the width W may be selected to match a particular intervertebral space. Each strut 120 also includes a length L, which extends from the first end 124 to the second 126. In one embodiment, the length L may be selected based upon the size of the intervertebral disc to be replaced. Each strut 120 also includes a thickness T. The intervertebral device 100 may include struts if different thicknesses T in the same device. The thickness T may be selected to fit a space between adjacent vertebrae. For instance, when the intervertebral device 100 is in the substantially closed state or zero inner volume state, the thickness T of adjacent strut 120 will approximate the space between adjacent vertebrae. The inner volume V may be calculated by taking the surface area of the anterior surface 108 or the posterior surface 118 and multiplying the surface area by the width W of the struts 120. The surface area of the anterior surface 108 or the posterior surface 118 may be calculated by taking the length L of each strut and calculating the surface area of the intervertebral device depending on how many struts are included in the intervertebral device 100. For example, if the intervertebral device includes 6 struts where each include the same length L, the area is calculated by a hexagonal structure with ((3*sqrt(3))/2) *L^2, where L is the length. In one embodiment, the surface area may be between about 200 mm2 and 700 mm2 in the expanded state, alternatively, between about 250 and 600 mm2, alternatively, between about 260 and 500 mm2.

In one embodiment, the longitudinal body member 122 generally includes a rectangular or square shape. Alternatively, the longitudinal body member 122 may assume alternative shapes and may include trapezoidal, hexagonal, polygonal, and the like. Alternatively, the anterior and posterior surfaces of the longitudinal body member 122 may be tapered or at an angle, such that the width W of the strut 120 varies along the length L of the strut. Such variation in the width W of the strut 120 may be preferable if the adjacent vertebra is deformed or at an angle with respect to the longitudinal axis 102 of the intervertebral device 100.

Figure 2C:
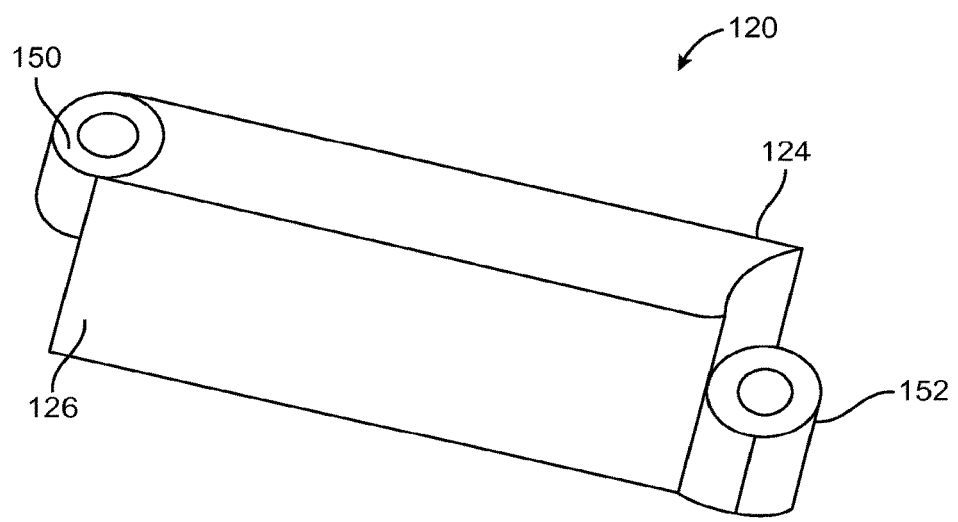
FIG. 2C is a perspective view of an alternative embodiment of the strut.
Figure 2D:
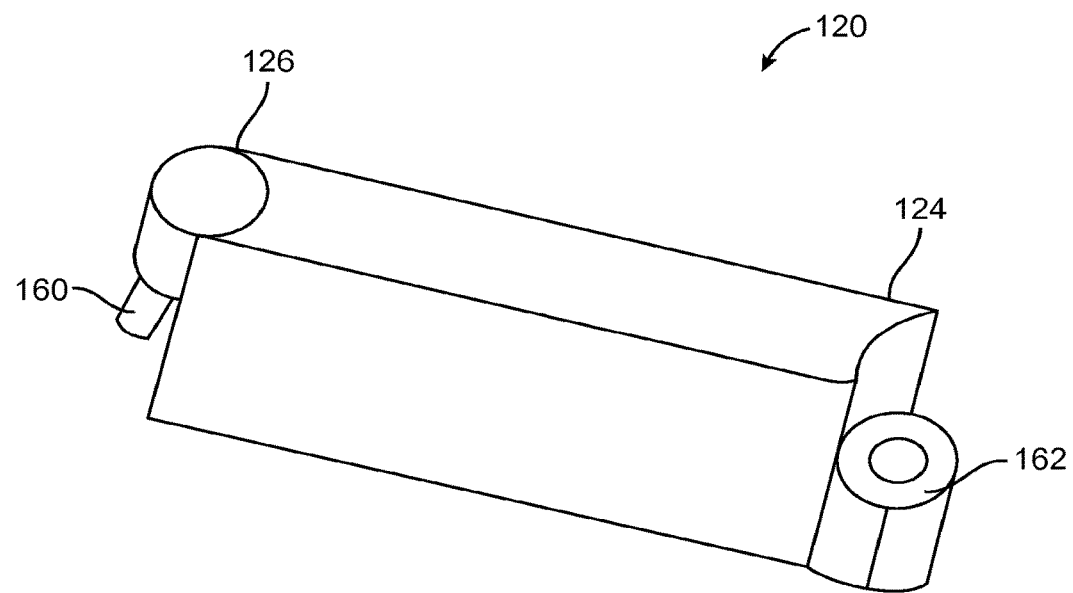
FIG. 2D is a perspective view of an alternative embodiment of the strut.

Alternative rotatable associations with adjacent struts are shown in FIGS. 2C-2D. In one embodiment, the strut 120 may be rotatably associated with adjacent struts by including a clearance hole 150 on the second end 126 and a capture whole 152 on the first end 124. Adjacent struts 120 are press fit to coaxially align the clearance hole 150 and capture hole 152, while a pin or screw passes through the clearance hole 150 and the capture hole 152. The capture hole may include a threaded portion to secure the pin or screw therein, which allows the strut 120 with the clearance hole 150 to rotate about an axis when the first end 124 is rotatably coupled with the second end 126. Alternatively, the pin or screw passing through the clearance hole and the capture hole 152 may lock the adjacent struts once adjacent struts have been rotated to a set angle.

In an alternative embodiment, as shown in FIG. 2D, the strut 120 may be rotatably associated with adjacent struts by including a protrusion 160 on the second end 126 and a mating hole 162 on the first end 124. The mating hole 162 may be flexed open to receive the protrusion 160 of an adjacent strut 120. Alternatively, the protrusion 160 may be a slotted circular member having radial flexibility provided by the slots and a distal end that is larger than a base end thereof. The mating hole 162 may include a corresponding inner shoulder such that upon insertion the protrusion 160 is compressed radially until the enlarged distal end passes over and is accommodated by the internal shoulders, thus permanently trapping the protrusion 160 within the mating hole 162. Once the mating hole 162 receives the protrusion 160, adjacent struts are rotatably associated about the respective first end 124 and second end 126. Any type of fastener, bolt, or screw may be used to lock the protrusion 160 with the mating whole 162 once adjacent struts are rotated at an angle with respect to each other.

Figure 3:
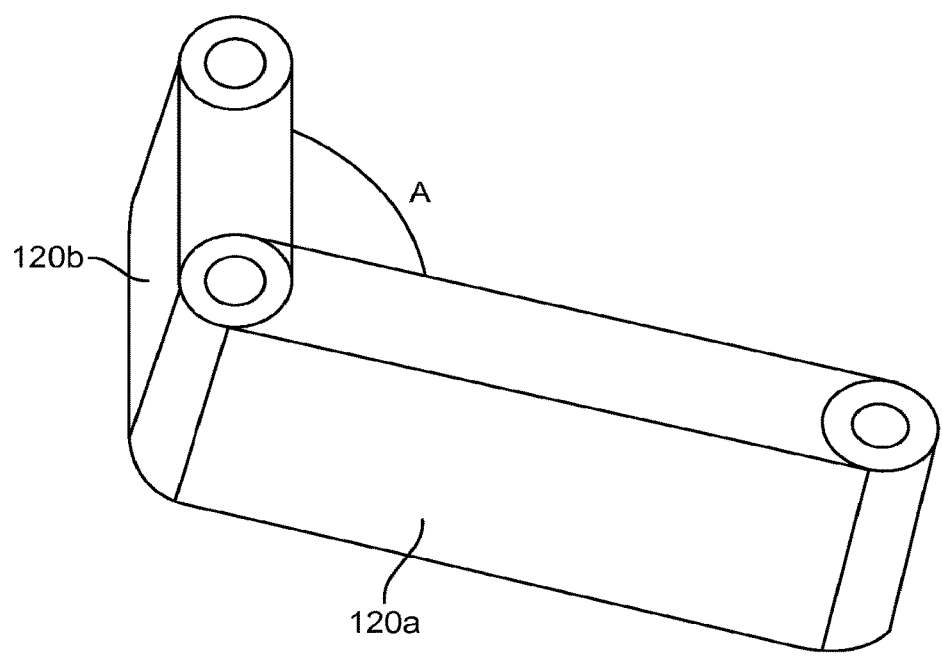
FIG. 3 is a perspective view of one embodiment of adjacent struts and angle A between rotatably associated struts.

As shown in FIG. 3, the adjacent struts 120 rotate or pivot to create an angle A between adjacent struts 120. The angle A may be selected upon the number of struts 120 used in the intervertebral device 100. Alternatively, the angle A may be selected upon the inner volume V to be attained for bone containment. For example, the angle A may be greater where the inner volume V is to be greater. Alternatively, the angle A between adjacent struts may be selected upon the number struts to be included in the intervertebral device. In one embodiment, the angle A between adjacent struts 120 is between about 30 and 270 degrees, alternatively, between about 60 and 240 degrees, alternatively, between about 90 and 200 degrees, alternatively, between about 120 and 170 degrees. As discussed above, the angle A may be locked or fastened once adjacent struts are rotated at an angle A of choice. Such locking or fastening of angle A maintains the inner volume V in a static or fixed state.

Figure 4A:
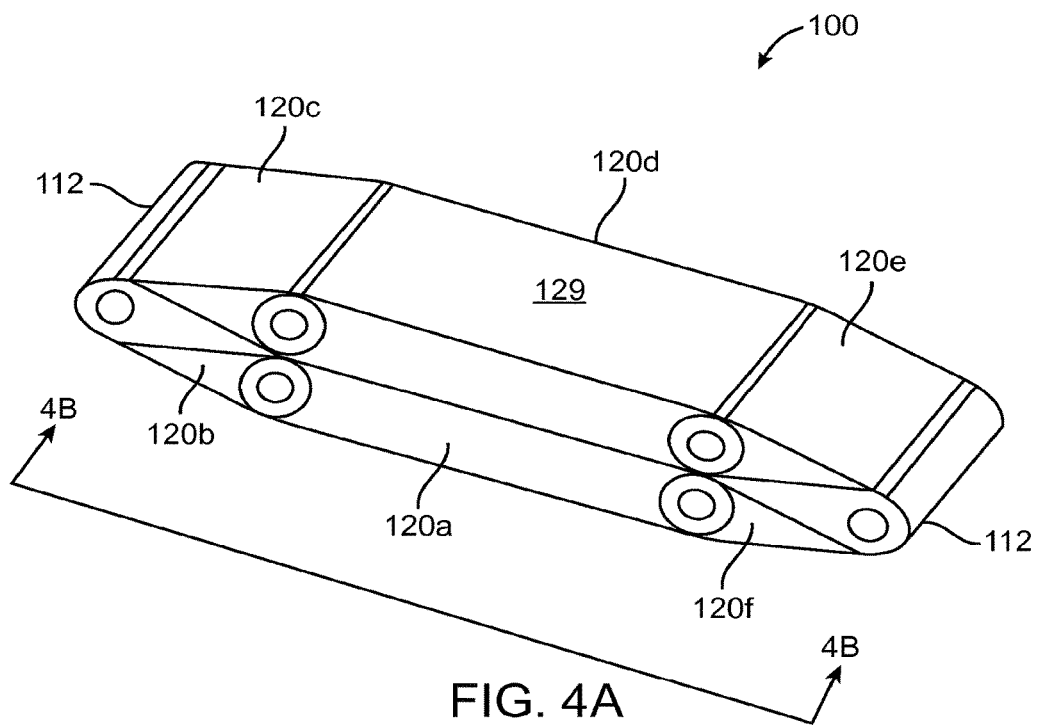
FIG. 4A is perspective view of one embodiment of the intervertebral device in the closed state or with a substantially zero inner volume V.
Figure 4B:
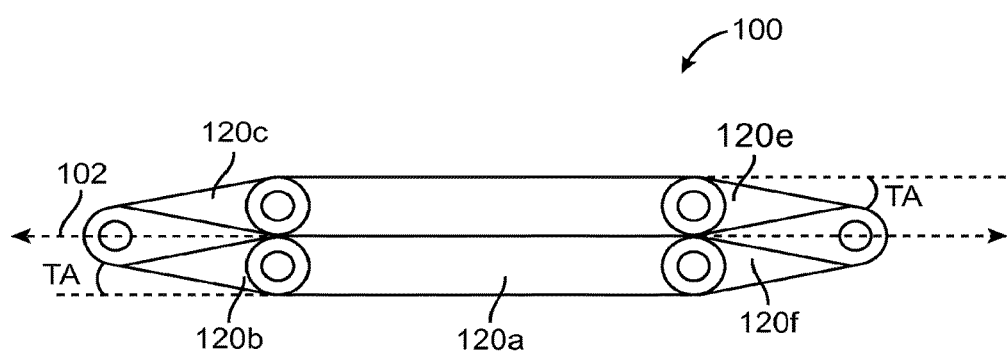
FIG. 4B is a top view of the intervertebral device in the closed state with a substantially zero inner volume V taken along lines 4B-4B as shown in FIG. 4A.

As shown in FIGS. 4A-B, the intervertebral device 100 may include a tapered portion on the proximal end 110 and distal end 110 when the intervertebral device 100 is in the closed state when the inner volume V is substantially zero. In this embodiment, the distal end 112 includes a second strut 120b and a third strut 120c, while the proximal end 110 includes a fifth strut 120e and a sixth strut 120f. The second strut 120b and the third strut 120c rotatably associate to the closed state when the interior faces of the second strut 120b and the third strut 120c abut each other and close thereupon on the distal end 112. The fifth strut 120e and the sixth strut 120f rotatably associate to the closed state when the interior faces of the fifth strut 120e and the sixth strut 120f abut each other and close thereupon on the proximal end 110. A first strut 120a and a fourth strut 120d are rotatably associated with the proximal end 110 and the distal end 112, such that the interior faces of the first strut 120a and the fourth strut 120d substantially abut each other when the intervertebral disc 100 is in the closed state. In one embodiment, the exterior faces 129 of the first and fourth strut 120a, 120d may include a coating or slick edge, as to assist in the insertion of the intervertebral device 100 through an incision point and/or sliding between adjacent vertebrae.

As shown in FIG. 4B, the fifth strut 120e, and the sixth strut 120f are tapered at an angle TA when the intervertebral disc 100 is in a zero inner volume V state or closed state. The angle TA is taken with respect to the first strut 120a and fourth strut 120d substantially parallel with the longitudinal axis 102 of the intervertebral device 100. In one embodiment, the tapered angle TA is between about 0 and 45 degrees, alternatively, between about 0 and 30 degrees, alternatively, between about 0 and 15 degrees, alternatively, between about 0 and 5 degrees. The tapered angle may be selected as to optimize the insertion of the intervertebral device 100 through an incision or retracted tissue point, as for minimally invasive during surgery, or to approximate a damaged intervertebral disc space to be wedged there within.

Figure 4C:
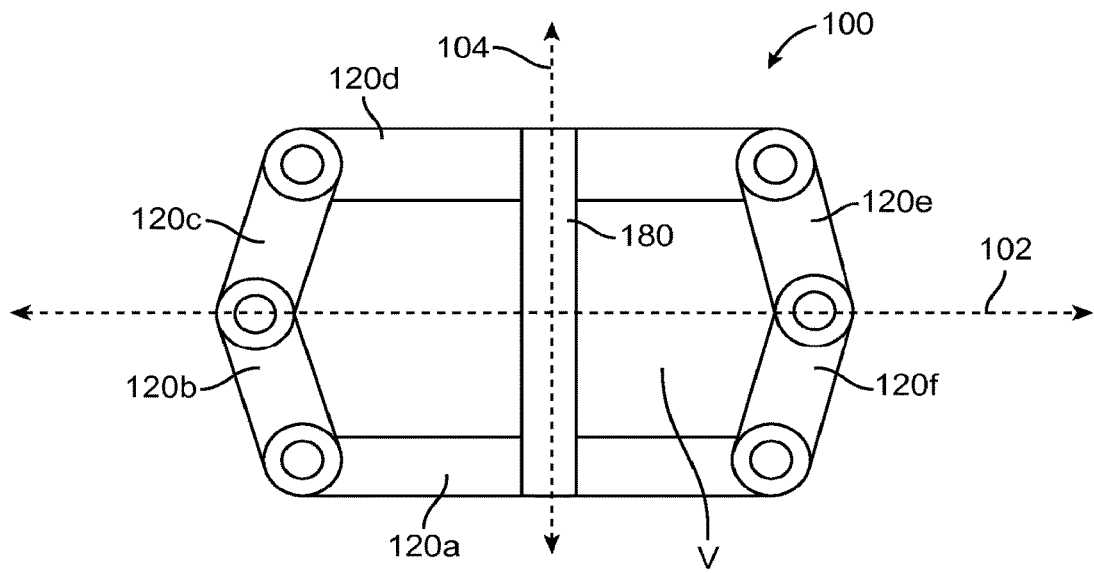
FIG. 4C is a top view of the intervertebral device in the expanded state with a locking mechanism.

In an alternative embodiment of the intervertebral disc 100, as shown in FIG. 4C, the intervertebral disc 100 includes a locking mechanism 180 to lock the intervertebral disc 100 when it is in the expanded state. The locking mechanism 180 may be a pin disposed generally along the transverse axis 104 spanning from the first strut 120a to the fourth strut 120d. Alternatively, the locking mechanism 140 may be a threaded pin, whereby at least one strut 120 includes a complimentary thread to receive the locking mechanism. Alternatively, the locking mechanism 180 may span from any opposing strut, generally along the longitudinal axis. The locking mechanism 180 may assist in keeping the intervertebral device 100 in an expanded state and to maintain a particular inner volume V. Alternatively, the first end 124 and the second end 126 of each strut may include a hinged locking mechanism within the rotatable portion of the first end 124 or the second end 126. The hinged locking mechanism may be secured in alternative or additional to the locking mechanism 140 to further lock down or fasten the rotatable associations on the first and second ends 124 and 126 of the struts 120.

Figure 5:
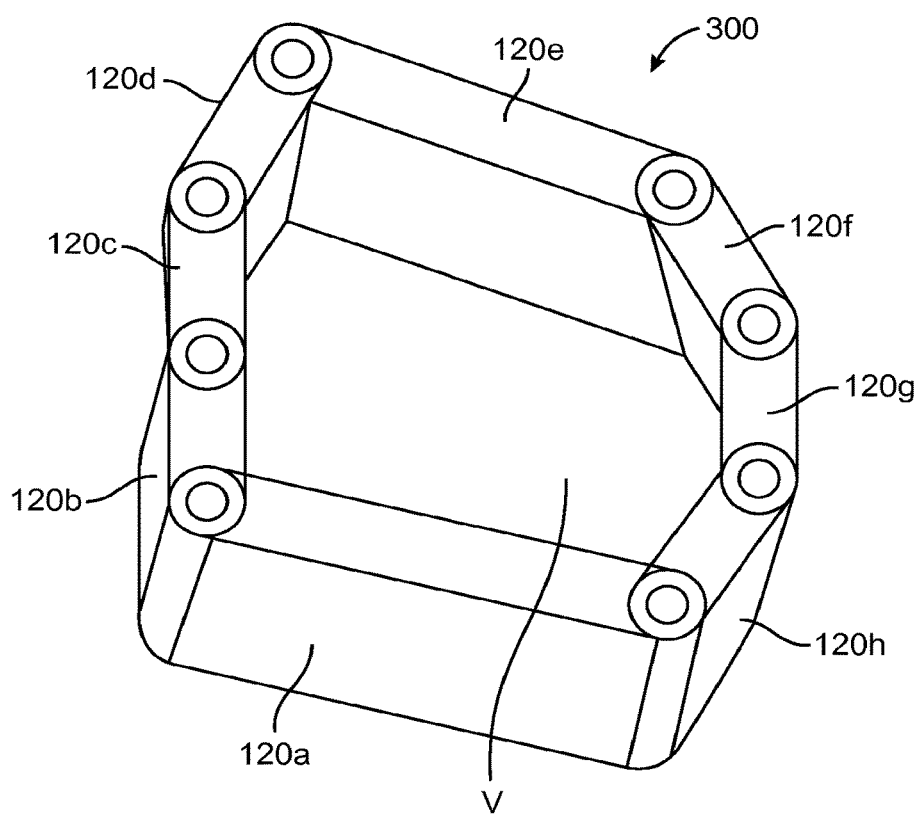
FIG. 5 is a perspective view of an alternative embodiment of the intervertebral device.

An alternative embodiment of the intervertebral device 300 is shown in FIG. 5. The intervertebral device 300 includes eight rotatably associated struts 120 and an inner volume V. The intervertebral device 300 includes a first strut 120a, a second strut 120b, a third strut 120c, a fourth strut 120d, a fifth strut 120e, a sixth strut 120f, a seventh strut 120g, and an eight strut 120h, wherein each adjacent strut is rotatably associated with the adjacent strut.

Figure 6A:
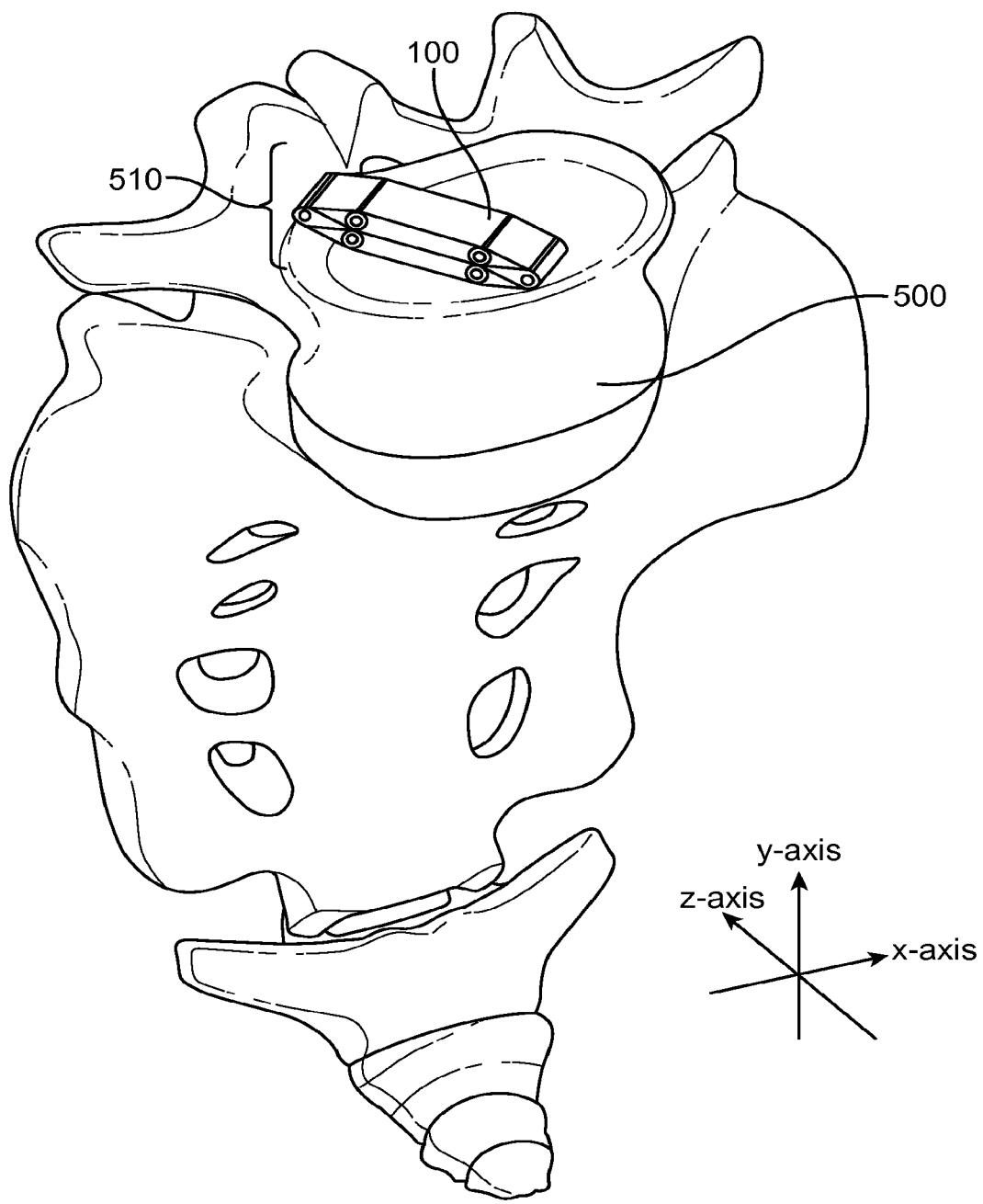
FIG. 6A is a perspective view of the intervertebral device and the vertebra, where the intervertebral device is being delivered to an intervertebral disc space rotated about its transverse axis.
Figure 6B:
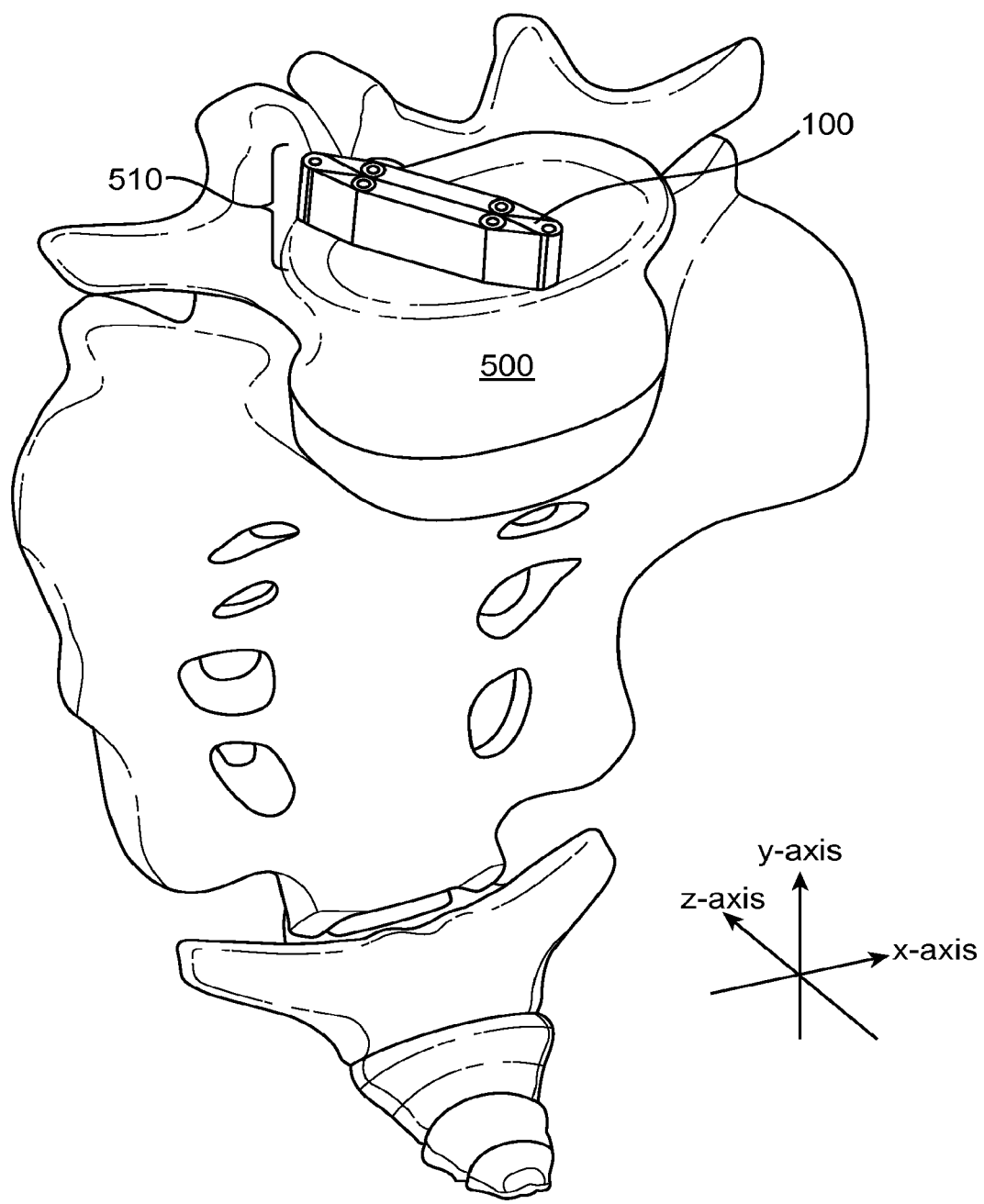
FIG. 6B is a perspective view of the intervertebral device and the vertebra, where the intervertebral device is rotated about its transverse axis once within the intervertebral disc space.
Figure 6C:
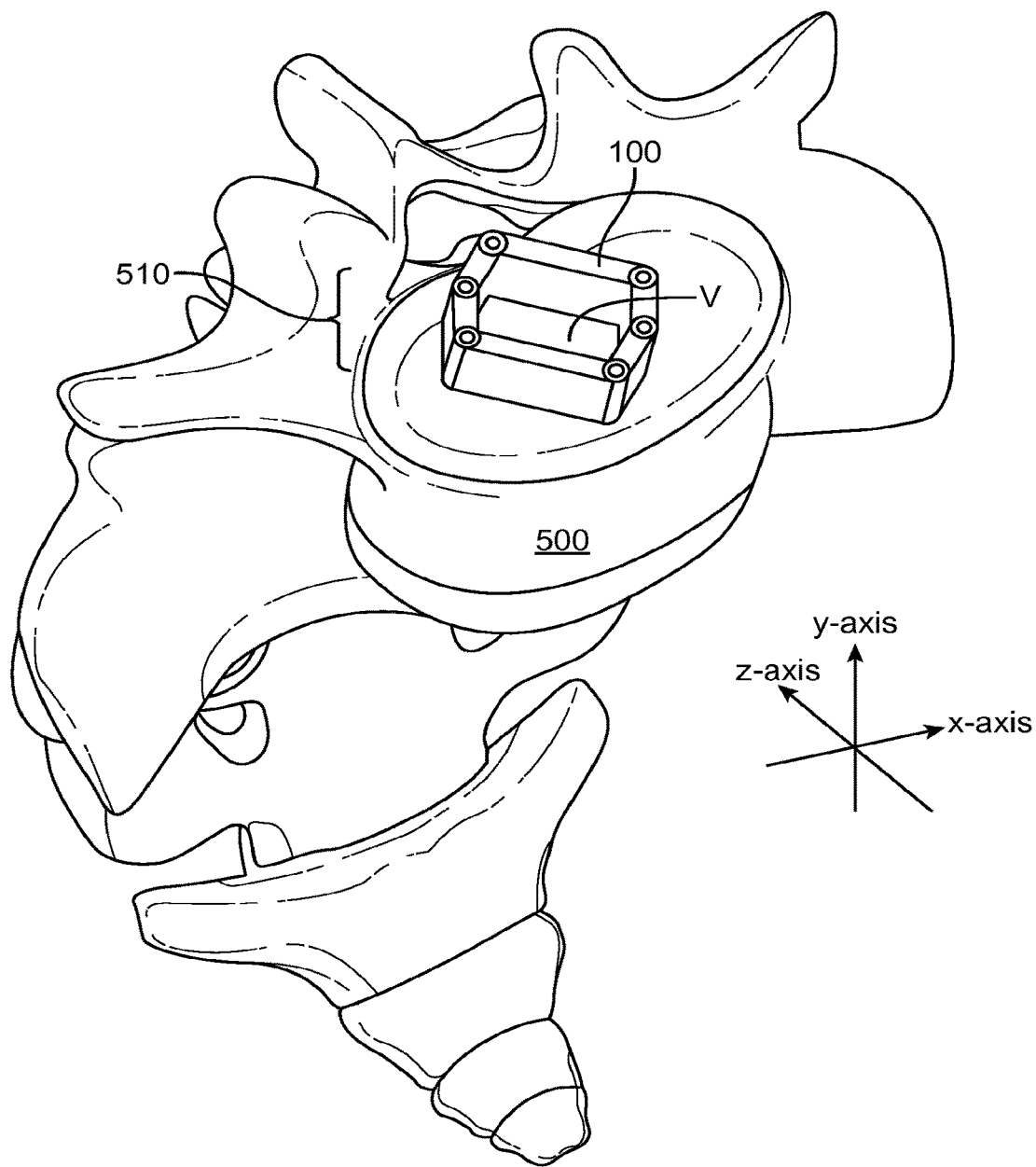
FIG. 6C is a perspective view of the intervertebral device and the vertebra, where the intervertebral device is expanded with an inner volume V once deployed in the intervertebral disc space for bone graft containment.

In operation, the first order of the surgical procedure is to prepare the intervertebral space by accessing the intervertebral disc space 510, removing a portion of the annulus, evacuating the nucleus, and then removing the cartilaginous endplates. The vertebrae 500 includes a cranio-caudal axis that is generally shown along the z-axis, a left-right axis that is generally shown along the x-axis, and a dorsoventral axis that is generally shown along the y-axis of FIGS. 6A-C. Once the intervertebral disc space 510 is prepared, the intervertebral device is connected to an instrumentation system for implantation and deployment of the intervertebral device 100 into the intervertebral disc space 510. Then, the intervertebral device is rotated about its transverse axis and is placed into the intervertebral disc space 510 with the width TT of the intervertebral device parallel to the vertebral endplates or the exterior faces 129 of the first and fourth struts 120a and 120d, as shown in FIG. 6A. Next, as shown in FIG. 6B, the intervertebral device is rotated 90 degrees about it's transverse axis to increase the height of the disc space and then the intervertebral device is expanded to the expanded state whereby the inner volume V is enclosed within the plurality of struts, such that the intervertebral device is "opened". Next, the intervertebral device increases the inner volume V and bone fusion-enhancing compounds are placed within the inner volume V, including but not limited to autologous bone, allograft bone, bone morphogenic protein (BMP), and/or any number of suitable biomaterials for bone graft containment, as shown in FIG. 6C.

Figure 7:
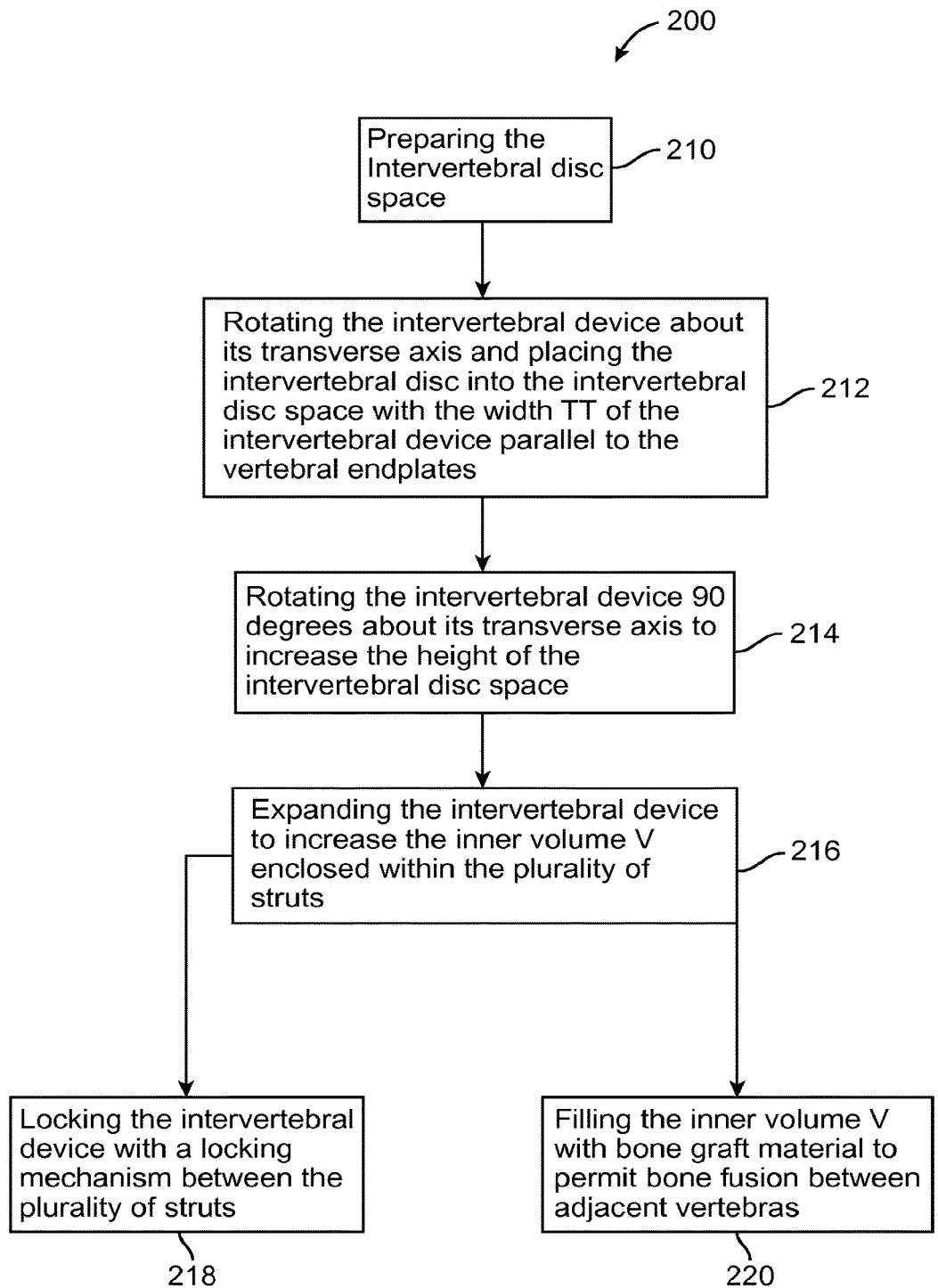
FIG. 7 is a schematic diagram for the method of using the intervertebral device.

A schematic diagram is shown in FIG. 7, for the method of using 200 the intervertebral disc 100. Step 210 is preparing the intervertebral disc space by removing a portion of the annulus, evacuating the nucleus, and then removing the cartilaginous endplates. Step 212 is rotating the intervertebral device about its transverse axis and placing the intervertebral disc into the intervertebral disc space with the width TT of the intervertebral device parallel to the vertebral endplates. Step 214 is rotating the intervertebral device 90 degrees about its transverse axis to increase the height of the intervertebral disc space. Step 216 is expanding the intervertebral device to increase the inner volume V enclosed within the plurality of struts, such that the intervertebral device is "opened". Optional Step 218 is locking the intervertebral device with a locking mechanism between the plurality of struts. Final Step 220 is filling the inner volume V with bone graft material to permit bone fusion between adjacent vertebrae.

As can be understood by one skilled in the art, the intervertebral device 100 and/or any of its components may have any size, shape, length, thickness, height, weight, or any other parameters. Such parameters may be selected by the surgeon (or other qualified professional) for performance of specific procedures. Further, the intervertebral device 100 and/or any of its components may be manufactured from metal, plastic, synthetic material, or other suitable materials, or any combination thereof. In one embodiment, the intervertebral device 100 is composed of titanium, nitinol, or stainless steel, pyrolitic carbon, any biocompatible material, or any medical grade polymer, such as Polyether ether ketone (PEEK).

In some embodiments, the struts 120 are included in various lengths and configurations, and may also include various features to accommodate different applications for the interspinous spacer. The struts 120 can be constructed of various materials to aid in radio translucency, strength, flexibility, and integration with anatomy, etc.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A method of using an intervertebral device, comprising the steps of:
   preparing an intervertebral disc space by removing a portion of the annulus, evacuating the nucleus, and then removing the cartilaginous endplates;
   rotating the intervertebral device about its transverse axis and placing the intervertebral disc into the intervertebral disc space with a width TI of the intervertebral device parallel to the vertebral endplates; the intervertebral device comprising:
      a plurality of struts, wherein each adjacent strut is rotatably associated with each adjacent strut to form a modifiable inner volume V for bone graft containment when the intervertebral device is in an expanded state, and
      whereby the inner volume V is enclosed by the plurality of struts
   rotating the intervertebral device 90 degrees about its transverse axis to increase the height of the intervertebral disc space;
   expanding the intervertebral device to increase the inner volume V enclosed within the plurality of struts, such that the intervertebral device is opened;
   locking the intervertebral device with a locking mechanism between the plurality of struts when the intervertebral device is expanded to increase the inner volume V, wherein the locking mechanism includes a hinged locking mechanism within one of the rotatable connections between adjacent struts configured to lock down or fasten the rotatable associations of the struts in the expanded state, wherein the hinged locking mechanism includes a screw, bolt, or fastener; and
   filling the inner volume V with bone graft material to permit bone fusion between adjacent vertebrae.

2. The method of claim 1, wherein each strut comprises a longitudinal body member extending from a first end and a second end of the strut; and wherein the first end includes a mating hole and the second end includes a protrusion, wherein the mating hole flexes open to receive the protrusion of an adjacent strut to rotatably associate adjacent struts about the first end and second end.

3. The method of claim 1, wherein each strut comprises a longitudinal body member extending from a first end and a second end of the strut and wherein the first end includes a capture hole and the second end includes a clearance hole, wherein adjacent struts are fit to coaxially align the clearance hole and capture hole, and a pin passes through the clearance hole and the capture hole to permit rotation about the first end and the second end of adjacent struts.

4. The method of claim 1, further comprising connecting the intervertebral device to an instrumentation system for implantation.

5. The method of claim 4, further comprising expanding the intervertebral device with the instrumentation system.

6. The method of claim 1, wherein intervertebral device is made from titanium, nitinol, stainless steel, pyrolitic carbon, any biocompatible material, or any medical grade polymer, such as Polyether ether ketone (PEEK).

7. The intervertebral device of claim 1, wherein the plurality of struts further comprises an anterior surface and a posterior surface, wherein at least one of the anterior surface or the posterior surface include a teethed surface.

8. The method of claim 1, wherein the inner volume V is substantially zero for delivery of the intervertebral device.

9. A method of using an expandable intervertebral device, comprising the steps of:
   preparing an intervertebral disc space by removing a portion of the annulus and evacuating the nucleus;
   connecting the expandable intervertebral device to an instrumentation system;
   placing the expandable intervertebral device in a closed state into the intervertebral disc space; the intervertebral device comprising:
      a plurality of struts, wherein each strut is rotatably connected with adjacent struts to form a modifiable inner volume V for bone graft containment when the intervertebral device is in an expanded state, and whereby the inner volume V is enclosed by the plurality of struts and the inner volume V is substantially zero when the plurality of adjacent struts rotates towards other struts;
      a hinged locking mechanism within one of the rotatable connections between adjacent struts configured to lock down or fasten the rotatable connection of the struts in the expanded state;
   expanding the expandable intervertebral device with the instrumentation system to the expanded state within the intervertebral disc space to increase the inner volume V enclosed within the plurality of struts, such that the intervertebral device is opened; and
   locking the expandable intervertebral device in the expanded state with the hinged locking mechanism; and
   disconnecting the expandable intervertebral device from the instrumentation system.

10. The method of claim 9, further comprising filling the inner volume V with bone graft material to permit bone fusion between adjacent vertebrae.

11. The method of claim 9, wherein each strut comprises a longitudinal body member extending from a first end and a second end of the strut; and wherein the first end includes a mating hole and the second end includes a protrusion; wherein the mating hole flexes open to receive the protrusion of an adjacent strut to rotatably associate adjacent struts about the first end and second end.

12. The method of claim 9, wherein each strut comprises a longitudinal body member extending from a first end and a second end of the strut, wherein the first end includes a capture hole and the second end includes a clearance hole, wherein adjacent struts are fit to coaxially align the clearance hole and capture hole, and a pin passes through the clearance hole and the capture hole to permit rotatable association about the first end and the second end of adjacent struts.

13. The method of claim 9, wherein placing the expandable intervertebral device in a closed state into the intervertebral disc space further includes:
   rotating the intervertebral device about a transverse axis and placing the intervertebral disc into the intervertebral disc space with a width TT of the intervertebral device parallel to the vertebral endplates; and rotating the intervertebral device 90 degrees about its transverse axis to increase the height of the intervertebral disc space.

14. The method of claim 9, wherein intervertebral device is made from titanium, nitinol, stainless steel, pyrolitic carbon, any biocompatible material, or any medical grade polymer, such as Polyether ether ketone (PEEK).

15. A method of using an expandable intervertebral device, comprising the steps of:
preparing an intervertebral disc spare by removing a portion of the annulus and evacuating the nucleus;
connecting the expandable intervertebral device to an instrumentation system;
placing the expandable intervertebral device in a closed state into the intervertebral disc space; the intervertebral device comprising:
  a plurality of struts, wherein each strut is rotatably connected with adjacent struts to form a modifiable inner volume V for bone graft containment when the intervertebral device is in an expanded state, and whereby the inner volume V is enclosed by the plurality of struts and the inner volume V is substantially zero when the plurality of adjacent struts rotates towards other struts;
  a hinged locking mechanism within one of the rotatable connections between adjacent struts configured to lock down or fasten the rotatable associations of the struts in the expanded state;
  wherein each strut comprises a longitudinal body member extending from a first end and a second end of the strut;
  wherein the first end includes a capture hole and the second end includes a clearance hole, wherein adjacent struts are fit to coaxially align the clearance hole and capture hole, and a pin passes through the clearance hole and the capture hole to permit rotatable association about the first end and the second end of adjacent struts; and
expanding the expandable intervertebral device with the instrumentation system to the expanded state within the intervertebral disc space to increase the inner volume V enclosed within the plurality of struts, such that the intervertebral device is opened; and
locking the expandable intervertebral device in the expanded state with the hinged locking mechanism; and
filling the inner volume V with bone graft material to permit bone fusion between adjacent vertebrae.

16. The method of claim 15, wherein placing the expandable intervertebral device in a closed state into the intervertebral disc space further includes:
rotating the intervertebral device about a transverse axis and placing the intervertebral disc into the intervertebral disc space with a width TT of the intervertebral device parallel to the vertebral endplates; and
rotating the intervertebral device 90 degrees about its transverse axis to increase the height of the intervertebral disc space.

17. The method of claim 15, wherein intervertebral device is made from titanium, nitinol, stainless steel, pyrolitic carbon, any biocompatible material, or any medical grade polymer, such as Polyether ether ketone (PEEK).

18. A method of using an intervertebral device, comprising the steps of:
preparing an intervertebral disc space by removing a portion of the annulus, evacuating the nucleus, and then removing the cartilaginous endplates;
rotating the intervertebral device about its transverse axis and placing the intervertebral disc into the intervertebral disc space with a width TT of the intervertebral device parallel to the vertebral endplates; the intervertebral device comprising:
  a plurality of struts, wherein each adjacent strut is rotatably associated with each adjacent strut to form a modifiable inner volume V for bone graft containment when the intervertebral device is in an expanded state, wherein each strut comprises a longitudinal body member extending from a first end and a second end of the strut; and wherein the first end includes a mating hole and the second end includes a protrusion, wherein the mating hole flexes open to receive the protrusion of an adjacent strut to rotatably associate adjacent struts about the first end and second end, and
  whereby the inner volume V is enclosed by the plurality of struts rotating the intervertebral device 90 degrees about its transverse axis to increase the height of the intervertebral disc space;
expanding the intervertebral device to increase the inner volume V enclosed within the plurality of struts, such that the intervertebral device is opened; and
filling the inner volume V with bone graft material to permit bone fusion between adjacent vertebrae.

19. The method of claim 18, further comprising locking the intervertebral device with a locking mechanism between the plurality of struts when the intervertebral device is expanded to increase the inner volume V.

20. The method of claim 19, wherein the locking mechanism includes a hinged locking mechanism within one of the rotatable connections between adjacent struts configured to lock down or fasten the rotatable associations of the struts in the expanded state.

21. The method of claim 20, wherein the hinged locking mechanism includes a screw, bolt, or fastener.

22. The method of claim 18, wherein each strut comprises a longitudinal body member extending from a first end and a second end of the strut and wherein the first end includes a capture hole and the second end includes a clearance hole, wherein adjacent struts are fit to coaxially align the clearance hole and capture hole, and a pin passes through the clearance hole and the capture hole to permit rotation about the first end and the second end of adjacent struts.

23. The method of claim 18, further comprising connecting the intervertebral device to an instrumentation system for implantation.

24. The method of claim 23, further comprising expanding the intervertebral device with the instrumentation system.

25. The method of claim 18, wherein intervertebral device is made from titanium, nitinol, stainless steel, pyrolitic carbon, any biocompatible material, or any medical grade polymer, such as Polyether ether ketone (PEEK).

26. The intervertebral device of claim 18, wherein the plurality of struts further comprises an anterior surface and a posterior surface, wherein at least one of the anterior surface or the posterior surface include a teethed surface.

27. The method of claim 18, wherein the inner volume V is substantially zero for delivery of the intervertebral device.

* * * * *